Figure 1:
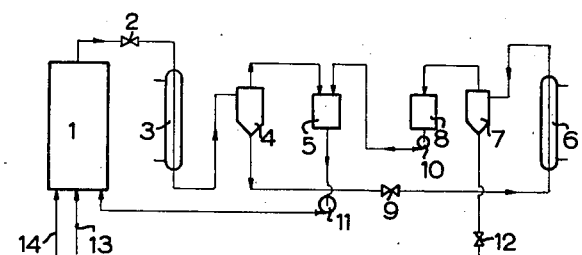

United States Patent [19]

Bongard

[11] 4,053,508
[45] Oct. 11, 1977

[54] PROCESS AND INSTALLATION FOR PREPARING UREA FROM AMMONIA AND CARBON DIOXIDE

[75] Inventor: Mathieu Bongard, Rotterdam, Netherlands

[73] Assignee: Stamicarbon, N.V., Geleen, Netherlands

[21] Appl. No.: 547,116

[22] Filed: Mar. 23, 1966

Related U.S. Application Data

[63] Continuation-in-part of Ser. No. 135,991, Sept. 6, 1961, abandoned.

[30] Foreign Application Priority Data

Sept. 5, 1960 Netherlands .................... 60255601

[51] Int. Cl.$^2$ .................................... C07C 126/00
[52] U.S. Cl. ................................... 260/555 A
[58] Field of Search .......................... 260/555

[56] References Cited
U.S. PATENT DOCUMENTS 3,172,911  3/1955  Mavrovic ............................ 260/555

OTHER PUBLICATIONS

Groggins, Unit Processes in Organic Syntheses, (fifth edition, 1958), p. 43.

*Primary Examiner*—James O. Thomas, Jr.
*Assistant Examiner*—A. Siegel
*Attorney, Agent, or Firm*—Cushman, Darby & Cushman

[57] ABSTRACT

A urea synthesis process is disclosed, wherein carbon dioxide and ammonium carbamate are reacted at elevated pressure to form urea, the resulting process stream is heated at reduced pressure to decompose ammonium carbamate, the off-gas from the ammonium carbamate decomposition is separated from the residual process stream (containing produce urea), and the off-gas is condensed to form an ammonium carbamate solution which is recycled to urea synthesis. A minimum amount of water in the condensate is recycled to the urea synthesis by taking an expanded gas-liquid mixture from a pressure reduction stage and directly separating the gas and liquid phases in such mixture without the application of heat thereto, thereafter heating the separated liquid phase to vaporize part of the liquid therein, and subjecting the resultant gas-mixture to separation, and condensing the gas phases obtained from both gas-liquid separations as condensate to be recycled to urea synthesis.

4 Claims, 4 Drawing Figures

PROCESS AND INSTALLATION FOR PREPARING UREA FROM AMMONIA AND CARBON DIOXIDE

This application is a continuation-in-part application of Ser. No. 135,991, filed Sept. 5, 1961, now abandoned.

The present invention relates to a process and an installation for preparing urea from ammonia and carbon dioxide, and more particularly to an improvement for reducing the amount of water in starting materials recirculated to the vessel in which urea is formed.

In this preparation, which is usually carried out by introducing liquid ammonia and carbon dioxide into an autoclave in which the reaction mixture is kept at a pressure of at least 160 atm. and at a temperature of at least 150° C, the reaction component first react to form ammonium carbamate. After that the ammonium carbamate is converted into urea and water, which conversion, however, does not proceed to completion; dependent on temperature and pressure a state of equilibrium is reached at a degree of conversion of 45 to 55%. This equilibrium can be shifted to the side of the urea formation by adding to the urea synthesis an amount of $NH_3$ exceeding the stoichiometric amount, in other words by employing a molar $NH_3$—$CO_2$-ratio greater than 2.

Also when carried out in this way the conversion of ammonium carbamate into urea and water is far from complete, so that the reaction mixture leaving the synthesis autoclave still contains ammonium carbamate in addition to water and urea, and, if a reaction mixture has a $NH_3$-$CO_2$-ratio greater than 2, free $NH_3$.

After expansion of this reaction mixture to a sufficiently low pressure, for instance a pressure of one atm. gauge, a gaseous mixture of $NH_3$ and $CO_2$ is obtained in addition to a urea solution with a concentration of approximately 75%.

As it is technically difficult — owing to the formation of solid ammonium carbamate at temperatures lower than 150° C — to retain the $NH_3$ and $CO_2$-containing mixture obtained in the expansion directly into the synthesis apparatus, it was thought sufficient for a long time to process the gas mixture to ammonium sulfate, ammonium nitrate or ammonium chloride and soda, whether or not after absorption in water. This method has the drawback that the urea production proper is coupled to the production of considerable amounts of by-product nitrogen-containing compounds.

To avoid this drawback several proposals have been made, which amounted to an absorption of the gas mixture in such a small quantity of water or another suitable solvent that the concentrated solution, or suspension, can be pumped back into the synthesis apparatus without having too adverse an effect on the conversion of ammonium carbamate into urea and water. See U.S. Pat. Nos. 1,898,093 and 2,116,881.

The problem involved in a process of this kind is that on the one hand it is desired to obtain a pure urea solution free of $NH_3$ and $CO_2$, which is only possible if the urea synthesis-reaction mixture is expanded to atmospheric or slightly super-atmospheric pressure, whereas on the other hand a much higher pressure has to be used in order that the $NH_3$ and $CO_2$ to be removed from the reaction mixture may be dissolved in a small quantity of water to form a concentrated ammoniacal ammonium carbamate solution.

This problem has been solved by allowing the urea synthesis-reaction mixture to expand in a few, two or three, pressure stages, the gases set free being condensed in each pressure stage; the condensate formed in the last pressure stage serves as condensation medium for the gases expelled in the penultimate pressure stage, and the condensate formed in this stage serves as condensation medium for the gases expelled in the preceding stage. In this way a urea solution which is practically free of $NH_3$ and $CO_2$ is discharged from the last pressure stage, while a concentrated ammoniacal ammonium carbamate solution or suspension, which is fed back to the urea synthesis autoclave, is obtained from the condenser in the first pressure stage. The apparatus required in each pressure stage consists of a device in which the urea solution is heated to form a liquid phase and a gas phase, a separator for separating the liquid phase from the gas phase, and a condenser for dissolving the gas phase in the condensate supplied to the condenser from the following pressure stage.

FIG. 1 is a diagram of this process; in the process shown in this figure the urea synthesis-reaction mixture is expanded in two pressure stages; in the first stage the reaction mixture issuing from the autoclave 1 under synthesis pressure is expanded via the expansion valve 2 to, for instance, 18 atm.; after this the mixture is heated in heater 3, the gas and liquid phases are separated in separator 4, and the liquid phase is expanded to the second pressure stage of, for instance, 3 atm. via expansion valve 9. Under this pressure the liquid-gas mixture obtained after expansion is passed through a heater 6 and after that separated in the liquid-gas separator 7. The resulting liquid phase, a urea solution which is practically free of $NH_3$ and $C_2$, can be discharged via valve 12 to be evaporated in vacuo for the recovery of crystals or prills.

The gases issuing from the gas-liquid separators 4 and 7 are condensed in condensers 5 and 8, respectively, the condensate formed in condenser 8 being pumped into condenser 5, in which a higher pessure prevails, by means of pump 10, while the condensate formed in condenser 5 is pumped back into the urea synthesis reactor by pump 11. $NH_3$ and $CO_2$ are admitted to the urea synthesis reactor via the conduits 13 and 14, respectively.

When this system is applied, a concentrated ammoniacal ammonium carbamate solution is ultimately fed back into the urea autoclave. As it is required that the amount of water in the autoclave is as small as possible in order that a good conversion yield may be obtained, it is advantageous if the water content in the ammonium carbamate solution or suspension to be returned is kept as low as possible.

It has been found, in accordance with the invention, that this can be realized in a simple way by omitting the direct heating to a higher temperature of the expanded mixture and the subsequent separation of the resulting liquid and gas phases, and instead leading this mixture after expansion and without preheating, through a preliminary separator and heating the resulting liquid phase, after this leading the gas-liquid mixture then formed through another liquid separator. It is found that in this case the water content of the gas phases is lower than with the old method, in which no preliminary separator is used.

Figure 2:
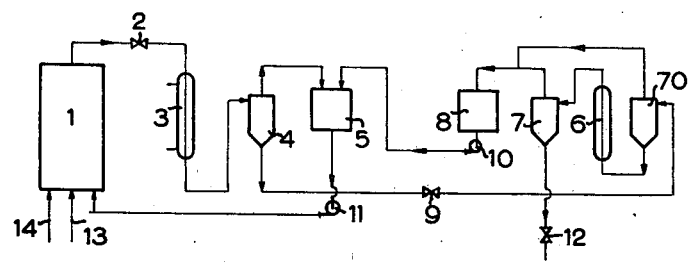
Figure 3:
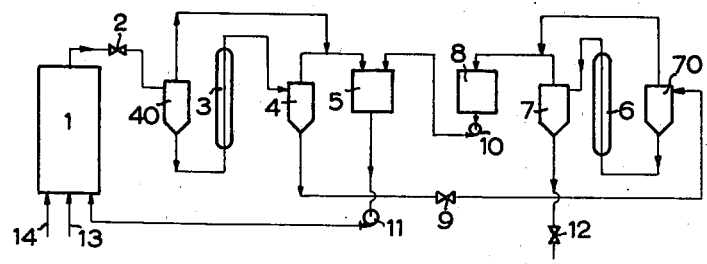
Figure 4:
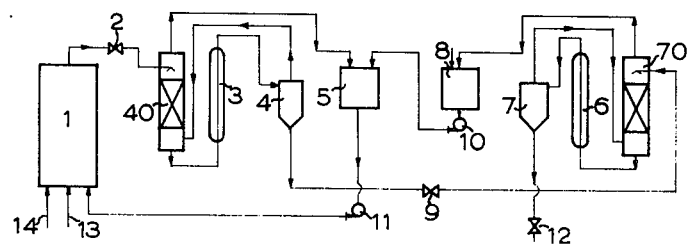

The FIGS. 2 - 4 are diagrams of the new process, FIG. 2 including a preliminary separator 70 in the last pressure stage, and FIG. 3 including a preliminary separator 40 in the first pressure stage and a preliminary separator 70 in the last pressure stage. The other reference numbers have the same meaning as in FIG. 1.

The following numerical examples serve to illustrate the invention.

EXAMPLE I

The process is carried out according to FIG. 1 and a pressure of 18 atm. and a temperature of 161° C prevail in separator 4 so that, the resulting mixture, after having been expanded to 3 atm. over valve 9, has a temperature of 110° C and shows the following composition:
- 16.8 moles of urea,
- 1.0 mole of $CO_2$
- 7.3 moles of $NH_3$
- 23.8 moles of $H_2O$.

This mixture is heated to 132° C in heater 6 and introduced into separator 7. The urea solution discharged from separator 7 contains:
- 16.8 moles of urea
- — moles of $CO_2$
- 1.0 mole of $NH_3$
- 16.9 moles of $H_2O$;

the gas phase escaping from the top of separator 7, and introduced into condenser 8 shows the following composition:
- 1.0 moles of $CO_2$
- 6.3 moles of $NH_3$
- 6.9 moles of $H_2O$.

EXAMPLE II

The process is carried out according to the diagram of FIG. 2, and the following liquid phase is dicharged from the preliminary separator 70 (temp. 110° C):
- 16.8 moles of urea
- 0.94 mole of $CO_2$
- 3.3 moles of $NH_3$
- 22.5 moles of $H_2O$ together with a gas phase of the follbwing composition:
- 0.06 mole of $CO_2$
- 4.0 moles of $NH_3$
- 1.3 moles of $H_2O$.

The liquid phase is heated to 132° C in heater 6 and the resulting mixture is introduced into separator 7. From this separator are discharged a liquid phase containing:
- 16.8 moles of urea
- — moles of $CO_2$
- 1.0 mole of $NH_3$
- 19.0 moles of $H_2O$ and a gas phase showing the following composition:
- 0.94 mole of $CO_2$
- 2.3 moles of $NH_3$
- 3.5 moles of $H_2O$ The gas phase from separators 7 and 70 are combined and introduced into condenser 8.

The compositions of the total gas mixtures introduced into condenser 8 according to the foregoing examples are as follows:

EXAMPLE I — FIG. 1
- 1.0 mole of $CO_2$
- 6.3 moles of $NH_3$
- 6.9 moles of $H_2O$,

EXAMPLE 2 — FIG. 2
- 1.0 mole of $CO_2$
- 6.3 moles of $NH_3$
- 4.8 moles of $H_2O$, the difference being 2.1 moles of $H_2O$ per mole of $CO_2$.

Owing to the amount of water being thus decreased, more concentrated solutions are formed in condenser 8, and in consequence of this a more concentrated solution is formed in condenser 5 so that a more concentrated ammonium carbamate solution is fed back to the urea synthesis reactor.

According to FIG. 1 the ammonium carbamate solution contains, for instance, 26.5% water, whereas with a preliminary separator in the second pressure stage according to FIG. 2, the water content is reduced to 25.1%

If a preliminary separator is also used in the first stage, as is indicated in FIG. 3, the water content is reduced to 19.4%.

Moreover, owing to the conversion yield in the urea synthesis reactor being increased, the amount of ammonium carbamate solution fed back is reduced, as a result of which smaller pumps may be used; there is also a saving of steam when the expanded gas mixture is heated in the two pressure stages. If the amount of ammonium carbamate solution fed back according to FIG. 1 is put at 100, it is reduced to 94 according to FIG. 2 and to 72 according to FIG. 3. For the amount of steam required, the figures are 100, 95 and 74, respectively.

In FIGS. 2 and 3 the preliminary gas-liquid separators 40 and 70 are indicated as simple separatory vessels provided with a feed line for the liquid-gas mixture, arranged between a liquid discharge line at the base and a gas discharge line at the top of the vessel. It is also possible, however, to apply a liquid gas separator of a more complicated design. A very satisfactory preliminary liquid-gas separator is a separator designed as a scrubber. The arrangement will then be as shown in FIG. 4 where the reference numbers denote the same parts as in FIGS. 1, 2 and 3. It will be noted that the gas phase recovered in separator 7 may be introduced into the lower end of the scrubber 70 to pass through the scrubber before flowing to condenser 8. synthesis, Of course, the gas flowing from separators 7 and 70 may be separately condensed rather than condensed together in a single condenser 8.

I claim:

1. In a process for the preparation of urea from ammonia and carbon dioxide in a urea synthesis zone at a pressure of at least 160 atmospheres and a temperature of at least 150° C wherein ammonia and carbon dioxide which have not been converted into urea are separated from the reaction product and recirculated back to the urea synthesis in the form of ammonium carbamate by steps including discharging the reaction mixture from the synthesis zone, expanding the thus discharged reaction mixture in a plurality of pressure stages operated at sequentially lower pressures and separating the gas and liquid phases after the expansion in each of said stages to yield a urea solution which is practically free of unreacted ammonia and carbon dioxide in the last stage, condensing the gas comprising ammonia, carbon dioxide and water from each pressure stage, the condensate formed in a lower pressure stage serving as condensation agent for the gas from a preceding pressure stage, and feeding back the condensate obtained in the first pressure stage to the urea synthesis, the improvement whereby a minimum amount of water is included in the condensate returned to said sunthesis, said improvement comprising the steps of taking the expanded gas-liquid mixture from a pressure stage and directly separating the gas and liquid phases (A) and (B), respectively, in said mixture without any application of heat thereto, thereafter heating the separated liquid phase (B) to vaporize part of the liquid therein, subjecting the resulting gas-liquid mixture to gas-liquid separation thereby obtaining gas phase (C) and liquid phase (D) and condensing the gas phases (A) and (C) obtained from both of said separations.

2. The process of claim 1, wherein the gas phases (A) and (C) obtained from both of said separations are condensed together.

3. The process of claim 1, wherein the gas phases (A) and (C) obtained from both of said separations are condensed togeher and are then used as the condensation agent to condense gas from a preceding pressure stage, the resulting condensate being fed back to the urea synthesis.

4. The process of claim 1, wherein the liquid phase D is the recovered urea solution which is essentially free of ammonia and carbon dioxide.

* * * * *

UNITED STATES PATENT OFFICE
CERTIFICATE OF CORRECTION

Patent No. 4,053,508      Dated October 11, 1977

Inventor(s) Mathieu Bongard

It is certified that error appears in the above-identified patent and that said Letters Patent are hereby corrected as shown below:

In "[63]" of the title page of the printed patent,

"Sept. 6, 1961" should read "Sept. 5, 1961".

Signed and Sealed this

Third Day of January 1978

[SEAL]

Attest:

RUTH C. MASON      LUTRELLE F. PARKER
Attesting Officer      Acting Commissioner of Patents and Trademarks